(12) United States Patent
Rosado

(10) Patent No.: US 9,737,203 B1
(45) Date of Patent: Aug. 22, 2017

(54) ANTI-SLIP SPECULUM GRIP AND METHODS OF USING SAME

(71) Applicant: Sulang Rosado, Chambersburg, PA (US)

(72) Inventor: Sulang Rosado, Chambersburg, PA (US)

( * ) Notice: Subject to any disclaimer, the term of this patent is extended or adjusted under 35 U.S.C. 154(b) by 0 days.

(21) Appl. No.: 15/438,851

(22) Filed: Feb. 22, 2017

(51) Int. Cl.
    A61B 17/02 (2006.01)
    A61B 1/06 (2006.01)
    A61B 1/303 (2006.01)
    A61B 1/32 (2006.01)

(52) U.S. Cl.
    CPC ............ *A61B 1/303* (2013.01); *A61B 1/32* (2013.01)

(58) Field of Classification Search
    CPC ... A61B 1/00142; A61B 1/00144; A61B 1/32; A61B 1/303; A61B 1/06; A61B 1/07; A61B 1/02; A61B 2017/00477; A61B 2017/00858; A61B 2017/00876; A61B 2017/0042; A61B 90/50; A61B 90/57; A61B 2090/306; A61B 2090/3612; A61B 2090/3514; A61B 2090/309; A61B 17/0218
    USPC ......................................... 600/213, 245, 220
    See application file for complete search history.

(56) References Cited

U.S. PATENT DOCUMENTS

| | | |
|---|---|---|
| 4,583,527 A | 4/1986 | Musicant et al. |
| 4,615,334 A | 10/1986 | Jaeger |
| 5,072,720 A * | 12/1991 | Francis .................. A61B 1/32 600/186 |
| 5,460,165 A | 10/1995 | Mayes |
| 5,709,646 A | 1/1998 | Lange |
| 2006/0084843 A1* | 4/2006 | Sommerich ............ A61B 17/02 600/210 |
| 2008/0242938 A1 | 10/2008 | Larkin |
| 2010/0331883 A1* | 12/2010 | Schmitz ............ A61B 10/0275 606/249 |
| 2014/0107405 A1* | 4/2014 | Hjelle ................. A61M 1/107 600/37 |

(Continued)

*Primary Examiner* — Pedro Philogene
(74) *Attorney, Agent, or Firm* — James R. McDaniel

(57) ABSTRACT

An anti-slip speculum grip for use in vaginal medical procedures, including a speculum including a speculum blade having an anterior and a posterior side and a speculum handle, and an anti-slip speculum grip operatively attached to a portion of the posterior side of the speculum blade, wherein the anti-slip speculum grip is further comprised of; an anti-slip speculum grip base having a first side and a second side, an adhesive layer located adjacent to the first side of the anti-slip speculum grip base and adjacent to the portion of the posterior side of the speculum blade in order to operatively attach the anti-slip speculum grip to the posterior side of the speculum blade, an x-ray detector device located between the anti-slip speculum grip base and the adhesive layer, a speculum grip textured side located on the second side of the anti-slip speculum grip base, wherein the speculum grip textured side is further comprised of; a plurality of raised areas arranged on the speculum grip textured side in a predetermined pattern, wherein the raised areas interact with vaginal tissues to provide absorptive friction between the vaginal tissues and the speculum thereby preventing the speculum from slipping out/falling out of a vaginal canal during a vaginal medical procedure.

16 Claims, 2 Drawing Sheets

(56) References Cited

U.S. PATENT DOCUMENTS

2014/0323811 A1\* 10/2014 DeSantis ................. A61B 1/06
600/213

\* cited by examiner

ANTI-SLIP SPECULUM GRIP AND METHODS OF USING SAME

FIELD OF THE INVENTION

The present invention is generally related to an anti-slip speculum grip. The grip keeps a metal speculum from slipping out/falling out of the vaginal canal or otherwise leaving the operation field during a medical procedure. The single use, disposable, anti-slip speculum grip is placed by its adherent side to the posterior side of the blade of the metal vaginal speculum prior to its use in the vagina. The foam-like material in contact with the vaginal tissues provides absorptive friction between the posterior of the vagina and the metal speculum thereby preventing the speculum from slipping out/falling out of the vaginal canal or otherwise leaving the operation field during a medical procedure.

BACKGROUND OF THE INVENTION

Prior to the present invention, as set forth in general terms above and more specifically below, it is known, to employ various types of speculums. See for example, U.S. Pat. No. 4,583,527 by Musicant et al., U.S. Pat. No. 4,615,334 by Jaeger, U.S. Pat. No. 5,072,720 by Francis et at, U.S. Pat. No. 5,460,165 by Mayes, U.S. Pat. No. 5,709,646 by Lange, and U.S. Patent Application Publication 2008/0242938 by Larkin. While these various speculums may have been generally satisfactory, there is nevertheless a need for a new and improved anti-slip speculum grip that would keep the metal speculum from slipping out/falling out of the vaginal canal or otherwise leaving the operation field during a medical procedure.

It is a purpose of this invention to fulfill these and other needs in the speculum art in a manner more apparent to the skilled artisan once given the following disclosure.

BRIEF SUMMARY OF THE INVENTION

A first aspect of the present invention is an anti-slip speculum grip for use in vaginal medical procedures, including a speculum including a speculum blade having an anterior and a posterior side and a speculum handle, and an anti-slip speculum grip operatively attached to a portion of the posterior side of the speculum blade, wherein the anti-slip speculum grip is further comprised of; an anti-slip speculum grip base having a first side and a second side, an adhesive layer located adjacent to the first side of the anti-slip speculum grip base and adjacent to the portion of the posterior side of the speculum blade in order to operatively attach the anti-slip speculum grip to the posterior side of the speculum blade, an x-ray detector device located between the anti-slip speculum grip base and the adhesive layer, a speculum grip textured side located on the second side of the anti-slip speculum grip base, wherein the speculum grip textured side is further comprised of; a plurality of raised areas arranged on the speculum grip textured side in a predetermined pattern, wherein the raised areas interact with vaginal tissues to provide absorptive friction between the vaginal tissues and the speculum thereby preventing the speculum from slipping out/falling out of a vaginal canal during a vaginal medical procedure.

In one embodiment of the first aspect of the present invention, the anti-slip speculum grip base includes a polymeric material.

In another embodiment of the first aspect of the present invention, the polymeric material includes a polymeric foam.

In another embodiment of the first aspect of the present invention, the polymeric foam is capable of absorbing blood and/or other bodily fluids that can be encountered during the vaginal medical procedure.

In another embodiment of the first aspect of the present invention, the adhesive layer includes any suitable, durable adhesive that is capable of adequately attaching anti-slip speculum grip to the portion of the posterior side of the speculum blade.

In still another embodiment of the first aspect of the present invention, the speculum grip textured side includes a polymeric material.

In an even further embodiment of the first aspect of the present invention, the polymeric material of the speculum grip textured side includes a polymeric foam.

In yet another embodiment of the first aspect of the present invention, the polymeric foam is capable of absorbing blood and/or other bodily fluids that can be encountered during the vaginal medical procedure and is capable of being formed into the plurality of raised areas.

In still another embodiment of the first aspect of the present invention, the plurality of raised areas includes a plurality of ridges.

A second aspect of the present invention is a speculum for use in vaginal medical procedures, including a speculum having a speculum blade including an anterior and a posterior side and a speculum handle, and an anti-slip speculum grip operatively attached to a portion of the posterior side of the speculum blade, wherein the anti-slip speculum grip is further comprised of; an anti-slip speculum grip base having a first side and a second side, an adhesive layer located adjacent to the first side of the anti-slip speculum grip base and adjacent to the portion of the posterior side of the speculum blade in order to operatively attach the anti-slip speculum grip to the posterior side of the speculum blade, an x-ray detector device located between the anti-slip speculum grip base and the adhesive layer, a speculum grip textured side located on the second side of the anti-slip speculum grip base, wherein the speculum grip textured side is further comprised of; a plurality of raised areas arranged on the speculum grip textured side in a predetermined pattern, wherein the raised areas interact with vaginal tissues to provide absorptive friction between the vaginal tissues and the speculum thereby preventing the speculum from slipping out/falling out of a vaginal canal during a vaginal medical procedure.

In one embodiment of the second aspect the present invention, the anti-slip speculum grip base includes a polymeric material.

In another embodiment of the second aspect of the present invention, the polymeric material includes a polymeric foam.

In another embodiment of the second aspect of the present invention, the polymeric foam is capable of absorbing blood and/or other bodily fluids that can be encountered during the vaginal medical procedure.

In another embodiment of the second aspect of the present invention, the adhesive layer includes any suitable, durable adhesive that is capable of adequately attaching the anti-slip speculum grip to the portion of the posterior side of the speculum blade.

In still another embodiment of the second aspect of the present invention, the speculum grip textured side includes a polymeric material.

In an even further embodiment of the second aspect of the present invention, the polymeric material of the speculum grip textured side includes a polymeric foam.

In yet another embodiment of the second aspect of the present invention, the polymeric foam of the speculum grip textured side is capable of absorbing blood and/or other bodily fluids that can be encountered during the vaginal medical procedure and is capable of being formed into the plurality of raised areas.

In still another embodiment of the second aspect of the present invention, the plurality of raised areas includes a plurality of ridges.

A third aspect of the present invention is a method of using an anti-slip speculum grip in a vaginal medical procedure, including the steps of: attaching an anti-slip speculum grip to a speculum, wherein the speculum includes a speculum blade having an anterior and a posterior side and a speculum handle; and the anti-slip speculum grip is operatively attached to a portion of the posterior side of the speculum blade, wherein the anti-slip speculum grip is further comprised of; an anti-sap speculum grip base having a first side and a second side; an adhesive layer located adjacent to the first side of the anti-slip speculum grip base and adjacent to the portion of the posterior side of the speculum blade in order to operatively attach the anti-slip speculum grip to the posterior side of the speculum blade; an x-ray detector device located between the anti-slip speculum grip base and the adhesive layer; a speculum grip textured side located on the second side, of the anti-slip speculum grip base, wherein the speculum grip textured side is further comprised of: a plurality of raised areas arranged on the speculum grip textured side in a predetermined pattern; and inserting the speculum blade and the anti-slip speculum grip into a vagina of a patient, wherein the raised areas interact with vaginal tissues to provide absorptive friction between the vaginal tissues and the speculum thereby preventing the speculum from slipping out/falling out of a vaginal canal during a vaginal medical procedure.

In one embodiment of the third aspect of the present invention, the method is further comprised of the step of removing and discarding the anti-slip speculum grip at a conclusion of the vaginal medical procedure in order to substantially eliminate cross contamination between patients.

The preferred anti-slip speculum grip, according to various embodiments of the present invention, offers the following advantages: ease of use; lightness in weight; durability; excellent slip resistance characteristics; ease of application; reduced risk of gross contamination of the operative field from fecal matter and fecal bacteria; reduced operating room time by providing operating room efficiency therefore reducing total operating room costs; the ability to absorb blood in the operative field which improves operative visibility thereby enhancing surgical precision and accuracy which leads to better patient safety and better surgical outcomes; the use of a single use/disposable pad which results in no cross contamination between patients; the ability to be detected by an x-ray detector; and secure placement of the metal vaginal speculum to keep it in place during the vaginal medical procedure. In fact, in many of the preferred embodiments, these advantages are optimized to an extent that is considerably higher than heretofore achieved in prior, known speculums.

BRIEF DESCRIPTION OF THE DRAWINGS

The above-mentioned features and steps of the invention and the manner of attaining them will become apparent, and the invention itself will be best understood by reference to the following description of the embodiments of the invention in conjunction with the accompanying drawings, wherein like characters represent like parts throughout the several views and in which.

DETAILED DESCRIPTION OF THE PREFERRED EMBODIMENTS OF THE INVENTION

Figure 1:
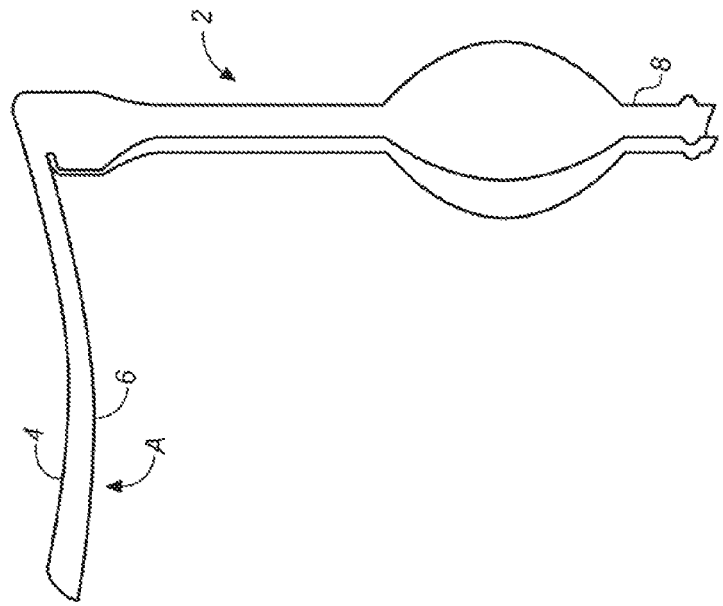
FIG. 1 is an isometric illustration of a speculum, according to the prior art.
Figure 2:
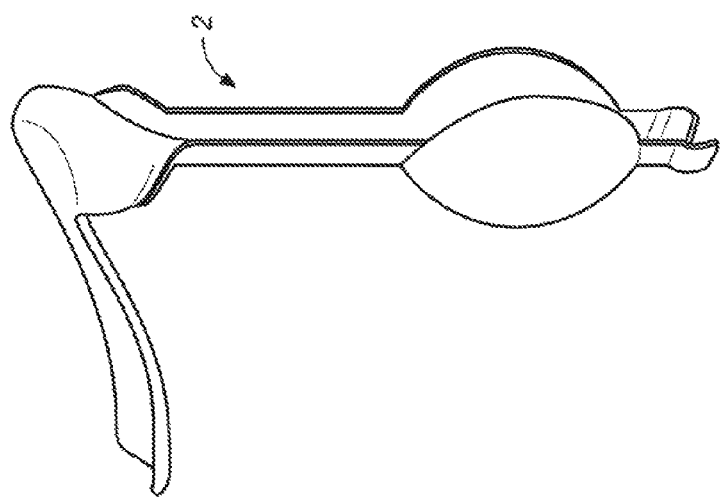
FIG. 2 is a side view of the speculum of FIG. 1, according to the prior art.

Referring now to FIGS. 1 and 2, there is illustrated a well-known speculum 2. It is known that currently all vaginal metal speculums 2 have the potential of slipping out of the vaginal canal and touching the rectal/anal area during gynecological vaginal procedures. Many times, the heavy weighted vaginal speculum 2 slips out and down into the rectal-anal area of the patient. If this is observed by the medical staff performing the procedure, the now contaminated speculum is removed from the surgical' field and the contaminated speculum 2 is replaced with a new sterile speculum 2.

It is further known that adding instruments not only adds to the surgical count but adds to the procedure time of the surgical case especially if a new sterile weighted speculum is not readily on hand. Furthermore, if the operating room circulator or other similar operating room personnel must leave the operating room to fine another clean, sterile speculum, this also will add to the procedure time because once the operating room circulator leaves the operating room to get another clean, sterile speculum, the personnel performing the operation may be forced to stop the operation and wait for the operating room circulator to return with hopefully the right instrument. Clearly, this is not desirable, since this adds to the total operating room time and this delay can be frustrating if the operation is a difficult one or unexpected bleeding occurs from a pedicle, or if the patient has risk factors where surgical efficiency is key to completing the medical procedure in a minimally invasive fashion.

Furthermore, it is known that there is unfortunately the risk where the vaginal speculum has indeed slipped into rectal-anal area and this has gone unnoticed during the medical procedure. In this case, if the "contaminated" speculum is used for the remainder of the case this can possibly lead to seeding of the vaginal cuff with fecal material and fecal bacteria which could result in post-operative vaginal cuff cellulitis, fever, vaginal cuff abscess, poor wound healing, readmission for intravenous (IV) antibiotics, and in some cases, vaginal cuff dehiscence. Clearly, this post-operative complication would most definitely lead to patient dissatisfaction and possible prolonged hospitalization which is highly undesirable.

Figure 3A:
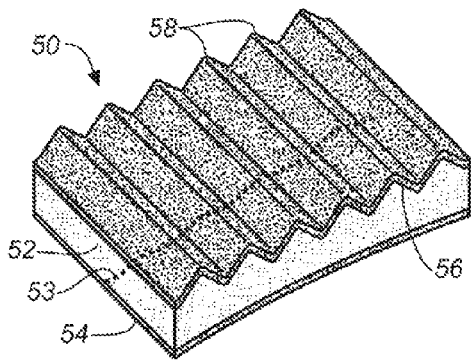
FIGS. 3A and 3B are schematic illustrations of the speculum grip, constructed according to the present invention.
Figure 3B:
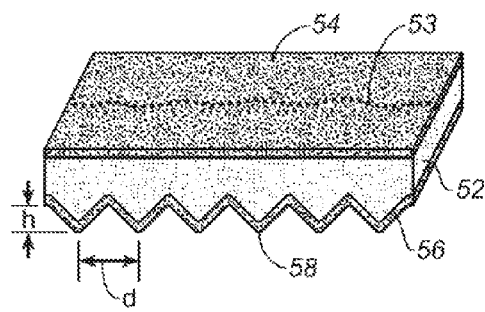

In order to address the shortcomings of the prior, known speculum 2, reference is made now to FIGS. 3A and 3B, where there is illustrated anti-slip speculum grip 50. As will be explained hereinafter in greater detail, the anti-slip speculum grip 50 keeps the metal speculum from slipping out/falling out of the vaginal canal or otherwise leaving the operation field during a medical procedure. The single use, disposable, anti-slip speculum grip 50 is placed by its adherent side 54 to the posterior side of the blade of the metal vaginal speculum 2 prior to its use in the vagina. The foam-like materials 52 and 56 in contact with the vaginal tissues provide absorptive friction between the posterior vagina and the metal speculum 2 thereby preventing the speculum 2 from slipping out/falling out of the vaginal canal or otherwise leaving the operation field during a medical procedure.

As shown in FIGS. 3A and 3B, there is illustrated anti-slip speculum grip 50 that is constructed according to the present invention. Anti-slip speculum grip 50 includes, in part, speculum grip base 52, x-ray detector device 53, speculum grip adhesive side 54, and speculum grip textured side 56.

With respect to speculum base 52, speculum base 52 is constructed of any suitable, lightweight, polymeric material such as a polycarbonate or cellulose foam that is durable and capable of absorbing blood and/or other bodily fluids that can be encountered during a variety of vaginal procedures. Preferably, the thickness of speculum base is such that speculum base 52 will be able to properly absorb the blood and/or other bodily fluids.

It is to be understood that there are at least two (2) different sizes of anti-slip speculum grip 50. This will allow for the anti-slip speculum grip 50 to be able to be attached to a variety of different vaginal speculums 2 having different types and sizes of speculum blades 4. As will be discussed in greater detail later, the type and size of the speculum blade 4 is determined prior to insertion into the patient's vagina and then the size of the anti-slip speculum grip 50 is selected and attached to the speculum blade 4. Preferably, the dimension ranges for the short (smaller) anti-slip speculum grip 50 are length: 6-8 cm (with the preferred length being 7 cm); width: 3-4 cm (with the preferred width being 3.5 cm); and depth: 0.25-0.75 cm (with the preferred depth being 0.5 cm). Regarding the long (larger) anti-slip speculum grip 50, the dimension ranges preferably are length 10-14 cm (with the preferred length being 12 cm); width: 3-4 cm (with the preferred width being 3.5 cm); and depth: 0.25-0.75 cm (with the preferred depth being 0.5 cm).

With respect to x-ray detector device 53, x-ray detector device 53, preferably is located between speculum base 52 and adhesive layer or side 54. Preferably, x-ray detector device 53 is located along a length of anti-slip speculum grip 50 and resembles a line or a strip. It is to be understood that x-ray detector device 53 is constructed of any suitable, durable, hypoallergenic material that is capable of having an x-ray detectable substance such as a radiopaque material conventionally applied such that the x-ray detector device 53 will be able to be easily detected by a conventional x-ray device. In this manner, the x-ray detector device will allow the anti-slip speculum grip 50 to be easily detected by the x-ray detector if the anti-slip speculum grip 50 inadvertently becomes dislodged from the speculum 2 during the medical procedure.

Regarding speculum grip adhesive layer or side 54, speculum grip adhesive layer or side 54 is located on the side of speculum base 52 that is to attached to the blade of speculum 2, as will be described in greater detail later. Speculum grip adhesive layer or side 54 includes an adhesive that is conventionally applied to speculum base 52. It is to be understood that the adhesive to be applied on speculum adhesive layer or side 54, preferably, is any suitable, durable, hypoallergenic adhesive that is capable of adequately attaching anti-slip speculum grip 50 to the blade 4 of the speculum 2 such as a polyacrylate or a synthetic rubber adhesive.

With respect to speculum grip textured side 56, speculum grip textured side 56 is located on the other side of speculum base 52. Preferably, speculum grip textured side 56 includes a plurality of raised areas 58 arranged on the speculum grip textured side 56 in a predetermined pattern. Regarding speculum grip textured side 56, speculum grip textured side 56, preferably is constructed of any suitable, durable, lightweight, polymeric material such as a polycarbonate or cellulose foam that is capable of absorbing blood and/or other bodily fluids that can be encountered during a variety of vaginal procedures and capable of being formed into raised areas 58. It is to be understood that raised areas 58 can include, but are not limited to, ridges, points, crests, elevations or other similar predetermined patterns/configurations. Preferably, raised areas 58 have a height (h) range of between 0.2 cm and 0.4 cm with the preferable height (h) being 0.3 cm. It is to be further understood that preferably, the distance (d) between adjacent raised areas 58 is a range of between 0.2 cm and 0.4 cm with the preferred distance (d) being 0.3 cm.

Regarding the orientation of raised areas 58, as shown in FIGS. 3A and 3B, raised areas 58 are located in a parallel direction to one side of anti-slip speculum grip 50. However, it is to be understood that the orientation of raised, areas 58 could run parallel to the other side of anti-slip speculum grip 50. Furthermore, the orientation of raised areas 58 could run in a diagonal orientation with respect to one side (or both sides-a crisscross orientation) of anti-slip speculum grip 50.

With respect to the number of raised areas 58 that are located on speculum grip textured side 56, the number of raised areas 58 can be varied. The important factor being that the number of raised areas 58 must be such that there are a sufficient number of raised areas 58 that will be available to interact with the vaginal tissues to provide absorptive friction between the posterior of the vagina and the metal speculum 2 thereby preventing the speculum 2 from slipping out/falling out of the vaginal canal or otherwise leaving the operation field during a medical procedure.

Figure 4:
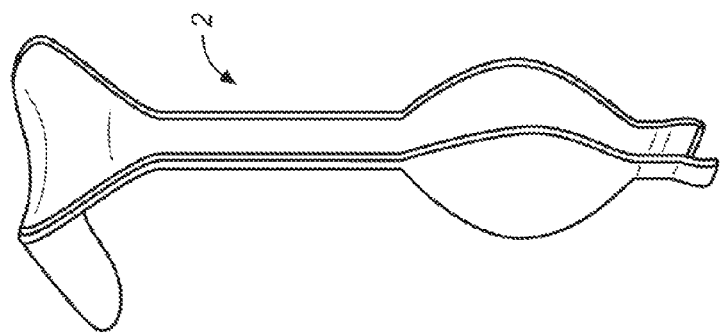
FIG. 4 is a side view of the speculum of FIG. 2, wherein the location of the placement of the anti-slip speculum grip is shown, according to the present invention.

Regarding FIG. 4, as discussed earlier, preferably, anti-slip speculum grip 50 is adhesively attached to speculum 2. As shown in FIG. 4, speculum 2 includes speculum blade 4 having a posterior side 6 and a speculum handle 8. As further shown in FIG. 4, the single use, disposable, anti-slip speculum grip 50 would be placed by its adherent side 54 to the posterior side of the blade of the metal vaginal speculum 2 in the area of arrow (A) on the posterior side 6 of speculum blade 4 prior to its use in the vaginal medical procedure.

Figure 5:
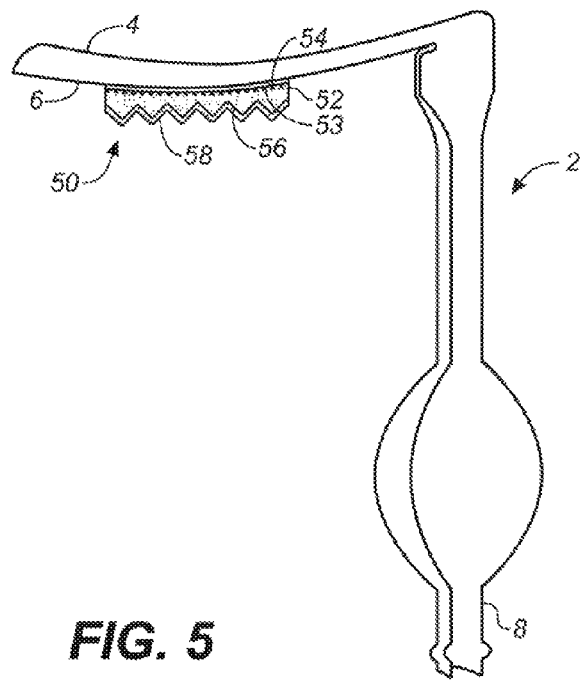
FIG. 5 is a schematic illustration, wherein the anti-slip speculum grip has been attached to the speculum of FIG. 4, according to the present invention.

With respect to FIG. 5, there is illustrated anti-slip speculum grip 50 attached to the posterior side 6 of speculum blade 4. A unique aspect of the present invention is that raised areas 58 interact with the vaginal tissues to provide absorptive friction between the posterior of the vagina and the metal speculum 2, thereby preventing the speculum 2 from slipping out/falling out of the vaginal canal or otherwise leaving the operation field during a medical procedure.

Another unique aspect of the present invention is that, in this configuration, anti-slip speculum grip 50 can be used to absorb blood and/or other bodily fluids that can be encountered during a variety of vaginal procedures. In this manner, the ability to absorb blood by anti-slip speculum grip 50 in the operative field improves operative visibility thereby enhancing surgical precision and accuracy which leads to better patient safety and better surgical outcomes With reference now to FIGS. 3A, 3B, 4 and 5, the operation and use of the anti-slip speculum grip 50 will now be discussed. As discussed earlier, once the size of the anti-slip speculum grip 50 is determined, the selected anti-slip speculum grip 50 is adhesively attached to by its adherent side 54 to the posterior side 6 of the blade 4 of the metal vaginal speculum 2 in the area of arrow (A) prior to its use in the vaginal medical procedure.

The speculum 2 having the attached anti-slip speculum grip 50 is then inserted into the vagina through the use of speculum handle 8 such that raised areas 58 interact with the vaginal tissues to provide absorptive friction between the posterior of the vagina and the metal speculum 2, thereby preventing the speculum 2 from slipping out/falling out of the vaginal canal or otherwise leaving the operation field during a medical procedure. Furthermore, anti-slip speculum grip 50 can be used to absorb blood and/or other bodily fluids that can be encountered during a variety of vaginal medical procedures.

A still further unique aspect of the present invention is that after anti-slip speculum grip 50 has been used in the medical procedure, the anti-slip speculum grip 50 is quickly and easily removed and properly discarded. In this manner, the use of the single use/disposable anti-slip speculum grip 50 results in no cross contamination between patients.

The preceding merely illustrates the principles of the invention. It will thus be appreciated that those skilled in the art will be able to devise various arrangements which, although not explicitly described or shown herein, embody the principles of the invention and are included within its spirit and scope. Furthermore, all examples and conditional language recited herein are principally intended expressly to be only for pedagogical purposes and to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention, as well as specific examples thereof, are intended to encompass both structural and functional equivalents thereof. Additionally, it is intended that such equivalents include both currently known equivalents and equivalents developed in the future, i.e., any elements developed that perform the same function, regardless of structure.

This description of the exemplary embodiments is intended to be read in connection with the figures of the accompanying drawing, which are to be considered part of the entire written description. In the description, relative terms such as "lower," "upper," "horizontal," "vertical" "above," "below," "up," "down," "top" and "bottom" as well as derivatives thereof (e.g., "horizontally," "downwardly," "upwardly," etc.) should be construed to refer to the orientation as then described or as shown in the drawing under discussion. These relative terms are for convenience of description and do not require that the apparatus be constructed or operated in a particular orientation. Terms concerning attachments, coupling and the like, such as "connected" and "interconnected," refer to a relationship wherein structures are secured or attached to one another either directly or indirectly through intervening structures, as well as both movable or rigid attachments or relationships, unless expressly described otherwise.

All patents, publications, scientific articles, web sites, and other documents and materials referenced or mentioned herein are indicative of the levels of skill of those, skilled in the art to which the invention pertains, and each such referenced document and material is hereby incorporated by reference to the same extent as if it had been incorporated by reference in its entirety individually or set forth herein in its entirety.

The applicant reserves the right to physically incorporate into this specification any and all materials and information from any such patents, publications, scientific articles, web sites, electronically available information, and other referenced materials or documents to the extent such incorporated materials and information are not inconsistent with the description herein.

The written description portion of this patent includes all claims. Furthermore, all claims, including all original claims as well as all claims from any and all priority documents, are hereby incorporated by reference in their entirety into the written description portion of the specification, and Applicant(s) reserve the right to physically incorporate into the written description or any other portion of the application, any and all such claims. Thus, for example, under no circumstances may the patent be interpreted as allegedly not providing a written description for a claim on the assertion that the precise wording of the claim is not set forth in haec verba in written description portion of the patent.

The claims will be interpreted according to law. However, and notwithstanding the alleged or perceived ease or difficulty of interpreting any claim or portion thereof, under no circumstances may any adjustment or amendment of a claim or any portion thereof during prosecution of the application or applications leading to this patent be interpreted as having forfeited any right to any and all equivalents thereof that do not form a part of the prior art.

All of the features disclosed in this specification may be combined in any combination. Thus, unless expressly stated otherwise, each feature disclosed is only an example of a generic series of equivalent or similar features.

It is to be understood that while the invention has been described in conjunction with the detailed description thereof, the foregoing description is intended to illustrate and not limit the scope of the invention, which is defined by the scope of the appended claims. Thus, from the foregoing, it will be appreciated that, although specific embodiments of the invention have been described herein for the purpose of illustration, various modifications may be made without deviating from the spirit and scope of the invention. Other aspects, advantages, and modifications are within the scope of the following claims and the present invention is not limited except as by the appended claims.

The specific methods and compositions described herein are representative of preferred embodiments and are exemplary and not intended as limitations on the scope of the invention. Other objects, aspects, and embodiments will occur to those skilled in the art upon consideration of this specification, and are encompassed within the spirit of the invention as defined by the scope of the claims. It will be readily apparent to one skilled in the art that varying substitutions and modifications may be made to the invention disclosed herein without departing from the scope and spirit of the invention. The invention illustratively described herein suitably may be practiced in the absence of any element or elements, or limitation or limitations, which is not specifically disclosed herein as essential. Thus, for example, in each instance herein, in embodiments or examples of the present invention, the terms "comprising", "including", "containing", etc. are to be read expansively and without limitation. The methods and processes illustratively described herein suitably may be practiced in differing orders of steps, and that they are not necessarily restricted to the orders of steps indicated herein or in the claims.

The terms and expressions that have been employed are used as terms of description and not of limitation, and there is no intent in the use of such terms and expressions to exclude any equivalent of the features shown and described or portions thereof, but it is recognized that various modifications are possible within the scope of the invention as claimed. Thus, it will be understood that although the present invention has been specifically disclosed by various embodiments and/or preferred embodiments and optional features, any and all modifications and variations of the concepts herein disclosed that may be resorted to by those skilled in the art are considered to be within the scope of this invention as defined by the appended claims.

The invention has been described broadly and generically herein. Each of the narrower species and sub-generic groupings falling within the generic disclosure also form part of the invention. This includes the generic description of the invention with a proviso or negative limitation removing any subject matter from the genus, regardless of whether or not the excised material is specifically recited herein.

It is also to be understood that as used herein and in the appended claims, the singular forms "a," "an," and the include plural reference unless the context clearly dictates otherwise, the term "X and/or Y" means "X" or "Y" or both "X" and "Y", and the letter "s" following a noun designates both the plural and singular forms of that noun. In addition, where features or aspects of the invention are described in terms of Markush groups, it is intended and those skilled in the art will recognize, that the invention embraces and is also thereby described in terms of any individual member or subgroup of members of the Markush group.

Other embodiments are within the following claims. Therefore, the patent may not be interpreted to be limited to the specific examples or embodiments or methods specifically and/or expressly disclosed herein. Under no circumstances may the patent be interpreted to be limited by any statement made by any Examiner or any other official or employee of the Patent and Trademark Office unless such statement is specifically and without qualification or reservation expressly adopted in a responsive writing by Applicants.

Although the invention has been described in terms of exemplary embodiments, it is not limited thereto. Rather, the appended claims should be construed broadly, to include other variants and embodiments of the invention, which may be made by those skilled in the art without departing from the scope and range of equivalents of the invention.

Other modifications and implementations will occur to those skilled in the art without departing from the spirit and the scope of the invention as claimed. Accordingly, the description hereinabove is not intended to limit the invention, except as indicated in the appended claims.

Therefore, provided herein are a new and improved anti-slip speculum grip. The preferred anti-slip speculum grip, according to various embodiments of the present invention, offers the following advantages: ease of use; lightness in weight; durability; excellent slip resistance characteristics; ease of application; reduced risk of gross contamination of the operative field from fecal matter and fecal bacteria; reduced operating room time by providing operating room efficiency, therefore reducing total operating room costs; the ability to absorb blood in the operative field which improves operative visibility, thereby enhancing surgical precision and accuracy which leads to better patient safety and better surgical outcomes; the use of a single use/disposable pad which results in no cross contamination between patients; the ability to be detected by an x-ray detector; and secure placement of the metal vaginal speculum to keep it in place during the vaginal procedure. In fact, in many of the preferred embodiments, these advantages of ease of use, lightness in weight, durability, excellent slip resistance characteristics, ease of application, reduced risk of gross contamination of the operative field from fecal matter and fecal bacteria, reduced operating room time by providing operating room efficiency, therefore reducing total operating room costs, the ability to absorb blood in the operative field which improves operative visibility, thereby enhancing surgical precision and accuracy which leads to better patient safety and better surgical outcomes, the use of a single use/disposable pad which results in no cross contamination between patients, the ability to be detected by an x-ray detector, and secure placement of the metal vaginal speculum to keep it in place during the vaginal medical procedure are optimized to an extent that is considerably higher than heretofore achieved in prior, known speculums.

I claim:

1. An anti-slip speculum grip for use in vaginal medical procedures, comprising:
   a speculum including a speculum blade having an anterior and a posterior side and a speculum handle; and
   an anti-slip speculum grip operatively attached to a portion of the posterior side of the speculum blade, wherein the anti-slip speculum grip is further comprised of;
   an anti-slip speculum grip base having a first side and a second side, wherein the anti-slip speculum grip base is capable of absorbing blood and/or other bodily fluids that can be encountered during the vaginal medical procedure;
   an adhesive layer located adjacent to the first side of the anti-slip speculum grip base and adjacent to the portion of the posterior side of the speculum blade in order to operatively attach the anti-slip speculum grip to the posterior side of the speculum blade;
   an x-ray detector device located between the anti-slip speculum grip base and the adhesive layer, wherein the x-ray detector device includes a string constructed of any suitable, durable, hypoallergenic material;
   a speculum grip textured side located on the second side of the anti-slip speculum grip base such that the speculum grip textured side is capable of absorbing blood and/or other bodily fluids that can be encountered during the vaginal medical procedure, wherein the speculum grip textured side is further comprised of:
   a plurality of raised areas arranged on the speculum grip textured side in a predetermined pattern, wherein the raised areas interact with vaginal tissues to provide absorptive friction between the vaginal tissues and the speculum thereby preventing the speculum from slipping out/falling out of a vaginal canal during a vaginal medical procedure.

2. The anti-slip speculum grip, according to claim 1, wherein the anti-slip speculum grip base is further comprised of:
   a polymeric material.

3. The anti-slip speculum grip, according to claim 2, wherein the polymeric material is further comprised of:
   polymeric foam.

4. The anti-slip speculum, grip, according to claim 1, wherein the adhesive layer is further comprised of:
   any suitable, durable adhesive that is capable of adequately attaching anti-slip speculum grip, to the portion of the posterior side of the speculum blade.

5. The anti-slip speculum grip, according to claim 1, wherein
the speculum grip textured side is further comprised of:
a polymeric material.

6. The anti-slip speculum grip, according to claim 5, wherein
the polymeric material is further comprised of:
polymeric foam.

7. The anti-slip speculum grip, according to claim 1, wherein the plurality of raised areas is further comprised of:
a plurality of ridges.

8. A speculum for use in vaginal medical procedures, comprising:
a speculum including a speculum blade having an anterior and a posterior side and a speculum handle; and
an anti-slip speculum grip operatively attached to a portion of the posterior side of the speculum blade, wherein the anti-slip speculum grip is further comprised of;
an anti-slip speculum grip base having a first side and a second side, wherein the anti-slip speculum grip base is capable of absorbing blood and/or other bodily fluids that can be encountered during the vaginal medical procedure;
an adhesive layer located adjacent to the first side of the anti-slip speculum grip base and adjacent to the portion of the posterior side of the speculum blade in order to operatively attach the anti-slip speculum grip to the posterior side of the speculum blade;
an x-ray detector device located between the anti-slip speculum grip base and the adhesive layer, wherein the x-ray detector device includes a string constructed of any suitable, durable, hypoallergenic material;
a speculum grip textured side located on the second side of the anti-slip speculum grip base such that the speculum grip textured side is capable of absorbing blood and/or other bodily fluids that can be encountered during the vaginal medical procedure, wherein the speculum grip textured side is further comprised of:
a plurality of raised areas arranged on the speculum grip textured side in a predetermined pattern, wherein the raised areas interact with vaginal tissues to provide absorptive friction between the vaginal tissues and the speculum thereby preventing the speculum from slipping out/falling out of a vaginal canal during a vaginal medical procedure.

9. The speculum, according to claim 8, wherein the anti-slip speculum grip base is further comprised of:
a polymeric material.

10. The speculum, according to claim 9, wherein the polymeric material is further comprised of:
polymeric foam.

11. The speculum, according to claim 8, wherein the adhesive layer is further comprised of:
any suitable, durable adhesive that is capable of adequately attaching anti-slip speculum grip to the portion of the posterior side of the speculum blade.

12. The speculum, according to claim 8, wherein the speculum grip textured side is further comprised of:
a polymeric material.

13. The speculum, according to claim 12, herein the polymeric material is further comprised of:
polymeric foam.

14. The speculum, according to claim 8, wherein the plurality of raised areas is further comprised of:
a plurality of ridges.

15. A method of using an anti-slip-speculum grip in a vaginal medical procedure, comprising the steps of:
attaching an anti-slip speculum grip to a speculum, wherein the speculum includes a speculum blade having an anterior and a posterior side and a speculum handle; and
the anti-slip speculum grip is operatively attached to a portion of the posterior side of the speculum blade, wherein the anti-slip speculum grip is further comprised of;
an anti-slip speculum grip base having a first side and a second side, wherein the anti-slip speculum grip base is capable of absorbing blood and/or other bodily fluids that can be encountered during the vaginal medical procedure;
an adhesive layer located adjacent to the first side of the anti-slip speculum grip base and adjacent to the portion of the posterior side of the speculum blade in order to operatively attach the anti-slip speculum grip to the posterior side of the speculum blade;
an x-ray detector device located between the anti-slip-speculum grip base and the adhesive layer, wherein the x-ray detector device includes a string constructed of any suitable, durable, hypoallergenic material;
a speculum grip textured side located on the second side of the anti-slip speculum grip base such that the speculum grip textured side is capable of absorbing blood and/or other bodily fluids that can be encountered during the vaginal medical procedure, wherein the speculum grip textured side is further comprised of:
a plurality of raised areas arranged on the speculum grip textured side in a predetermined pattern; and
inserting the speculum blade and the anti-slip speculum grip into a vagina of a patient, wherein the raised areas interact with vaginal tissues to provide absorptive friction between the vaginal tissues and the speculum thereby preventing the speculum from slipping out/falling out of a vaginal canal during a vaginal medical procedure.

16. The method of using the anti-slip speculum grip, according to claim 15, wherein the method is further comprised of the step of:
removing and discarding the anti-slip speculum grip at a conclusion of the vaginal medical procedure in order to substantially eliminate cross contamination between patients.

* * * * *